(12) United States Patent
Nitzan

(10) Patent No.: US 7,544,168 B2
(45) Date of Patent: Jun. 9, 2009

(54) MEASURING SYSTOLIC BLOOD PRESSURE BY PHOTOPLETHYSMOGRAPHY

(75) Inventor: Meir Nitzan, Mizrah Binyamin (IL)

(73) Assignee: Jerusalem College of Technology, Jerusalem (IL)

( * ) Notice: Subject to any disclaimer, the term of this patent is extended or adjusted under 35 U.S.C. 154(b) by 623 days.

(21) Appl. No.: 10/952,815

(22) Filed: Sep. 30, 2004

(65) Prior Publication Data

US 2006/0074322 A1    Apr. 6, 2006

(51) Int. Cl.
*A61B 5/02* (2006.01)

(52) U.S. Cl. .................. 600/495; 600/485; 600/490; 600/500

(58) Field of Classification Search .......... 600/495, 600/502, 507
See application file for complete search history.

(56) References Cited

U.S. PATENT DOCUMENTS

| | | | |
|---|---|---|---|
| 4,030,485 A | 6/1977 | Warner | |
| 4,418,700 A | 12/1983 | Warner | |
| 4,907,596 A | 3/1990 | Schmid et al. | |
| 4,928,692 A * | 5/1990 | Goodman et al. | 600/324 |
| 5,054,493 A | 10/1991 | Cohn et al. | |
| 5,140,990 A | 8/1992 | Jones et al. | |
| 5,237,997 A | 8/1993 | Greubel et al. | |
| 5,316,008 A | 5/1994 | Suga et al. | |
| 5,339,822 A * | 8/1994 | Taylor et al. | 600/513 |
| 5,857,975 A | 1/1999 | Golub | |
| 5,865,755 A | 2/1999 | Golub | |
| 6,120,459 A * | 9/2000 | Nitzan et al. | 600/493 |
| 6,280,390 B1 | 8/2001 | Akselrod et al. | |
| 6,527,725 B1 | 3/2003 | Inukai et al. | |
| 2003/0236451 A1 * | 12/2003 | El-Nokaly et al. | 600/300 |

FOREIGN PATENT DOCUMENTS

EP    0443267    8/1991

\* cited by examiner

*Primary Examiner*—Patricia C Mallari
(74) *Attorney, Agent, or Firm*—Mark M. Friedman

(57) ABSTRACT

The present invention relates to cuff-based method for the measurement of systolic blood pressure (SBP) by measuring photoplethysmographic (PPG) signals in peripheral blood vessels distal to the cuff and to a method for cuffless measurement of SBP by analyzing PPG signals in peripheral blood vessels, after suitable calibration by the cuff-based PPG method for the measurement of SBP.

24 Claims, 5 Drawing Sheets

MEASURING SYSTOLIC BLOOD PRESSURE BY PHOTOPLETHYSMOGRAPHY

FIELD AND BACKGROUND OF THE INVENTION

Figure 1:
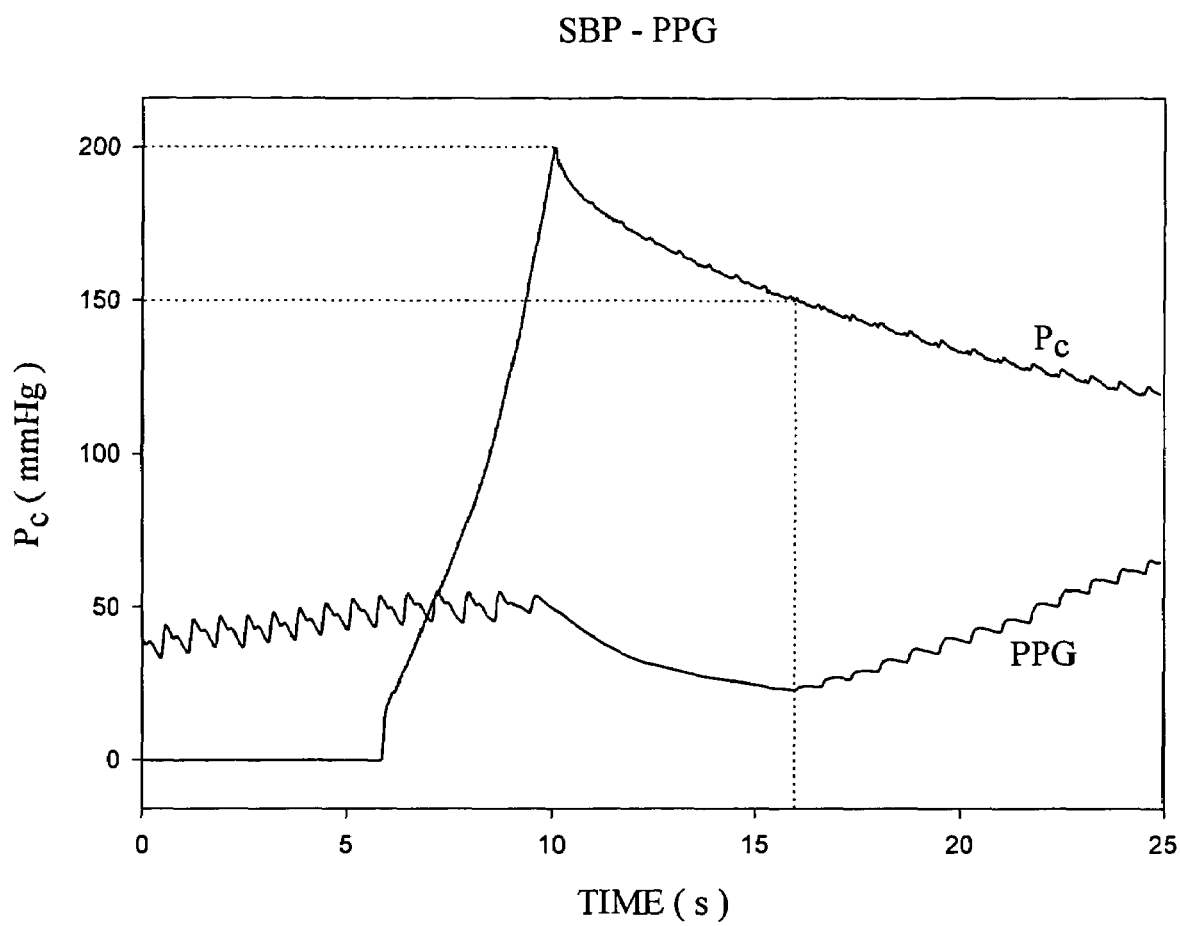

The present invention relates to cuff-based method for the measurement of systolic blood pressure (SBP) by measuring photoplethysmographic (PPG) signals in peripheral blood vessels distal to the cuff and to a method for cuffless measurement of SBP by analyzing PPG signals in peripheral blood vessels, after suitable calibration by the cuff-based PPG method for the measurement of SBP.

GENERAL BACKGROUND

Blood Pressure Meters for Single Measurements

The assessment of the arterial blood pressure has both physiological and clinical significance, and tremendous efforts have been applied to the development of a reliable noninvasive blood pressure (NIBP) meters. Manual sphygmomanometry is based on fast inflation of an external cuff to above the systolic blood pressure and audible detection of Korotkoff sounds during the subsequent slow deflation period and is considered to be the most accurate method, to which other methods should be compared. Manual sphygmomanometry is prone to several sources of error, which include insufficient hearing acuity of the user and behavioral factors such as the presence of a physician (white coat hypertension).

Some of these errors are avoided when automatic measurement of the blood pressure is performed, and several methods have been suggested for automatic NIBP measurement. The most widely used method is oscillometry, which together with the automatic auscultatory method account for almost all NIBP meters currently in use. The accuracy of the available automatic NIBP meters is low, as can be deduced from the standards imposed by the Association for the Advancement of Medical Instrumentation (AAMI) and the British Hypertension Society (BHS). The AAMI standards require that the mean difference between the SBP (or DBP) values measured by the manual sphygmomanometer and the tested automatic device is below 5 mmHg, and that the standard deviation of the differences is below 8 mmHg. According to these standards a tested automatic device for which 5% of the examinations differ from the reference device by more than 15 mmHg is acceptable. Such low accuracy is permitted because the known methods for automatic NIBP meters are not capable of providing measurements of higher accuracy.

SBP can also be measured through a photoplethysmographic (PPG) sensor distal to a pressure cuff, which is inflated to above SBP value and then slowly deflated. The PPG signal disappears for cuff pressure above SBP value and reappears when the cuff pressure decreases to below SBP value. The detection of the PPG pulses can be done either automatically or through inspection, and in our studies it was found that both techniques yield accuracy higher than that obtained by oscillometry: the standard deviation of the differences from manual sphygmomanometer was 4-5 mmHg.

As seen later, an accurate cuff-based method for blood pressure measurement is required for calibration of cuffless method for blood pressure monitoring, based on the analysis of PPG signal and an automatic cuff-based method for blood pressure measurement is required when the blood pressure is monitored at home. The cuff-based automatic SBP meter, which uses the PPG sensor, seems to be appropriate for the required at-home calibration.

The Clinical Significance Cuffless Monitoring

Long-term NIBP monitoring is of great importance for several clinical applications, such as 24 h ambulatory NIBP monitoring and telemedicine. 24 h ambulatory NIBP monitoring can provide information regarding the spontaneous changes in blood pressure and requires blood pressure measurement every 20-30 min, during the 24 h period. Telemedicine is a fast growing clinical modality, enabling ambulatory supervision of home-patients for months.

The use of the cuff-based methods for the multiple measurements of blood pressure in 24 h ambulatory monitoring and in telemedicine is limited because the process of cuff inflation and subsequent slow deflation is inconvenient, involves constriction of arteries, and requires long time of measurement. There is therefore need for cuffless blood pressure monitor for use in hospital and at home.

Prior Work

The technique for cuffless blood pressure monitoring should be based on non-invasive and cuffless measurement of some cardiovascular parameters, which are physiologically related to blood pressure. Even if adequate correlation is found between these cardiovascular parameters and SBP or DBP it is not yet certain that the absolute value of SBP or DBP can be extracted from the values of the physiological parameters. In this case initial calibration by a cuff-based method might solve the problem.

Several noninvasive techniques provide parameters, which are closely related to cardiovascular parameters and consequently might correlate with arterial blood pressure. In particular photoplethysmography (PPG)—the measurement through optical means of the cardiac-induced pulsatile changes in tissue blood volume—is a simple means for measuring various cardiovascular parameters, which correlate with arterial blood pressure, such as heart rate, pulse wave velocity and tissue blood volume changes. Many inventors suggested PPG for cuffless measurement of arterial blood pressure.

Warner in a US patent (U.S. Pat. No. 4,030,485, 1977) described a method for monitoring of systolic blood pressure from the differentiated PPG signal at the beginning of diastole, assuming that the arterial pressure is proportional to the rate of change of the microvascular blood volume. In another US patent Warner (U.S. Pat. No. 4,418,700, 1983) described a method for monitoring systolic and diastolic blood pressure from several parameters of a cyclic curve representing tissue blood volume: the maximum and minimum of each cycle of the curve, and the value of the signal at maximum slope. Both techniques use single PPG device.

Schmid in a US patent (U.S. Pat. No. 4,907,596, 1990) described a method for continuous monitoring of diastolic blood pressure based on the time intervals between peaks of the ECG signal and pulse beats detected by the pulse beat detector, using the fact that pulse beat transit time varies with the blood pressure. The blood pressure meter is initially calibrated by sphygmomanometry.

Jones et al. in a US patent (U.S. Pat. No. 5,140,990, 1992) described a method for continuous monitoring of systolic and diastolic blood pressure based on PPG measurements by a single PPG device. SBP and/or DBP are determined from the arterial blood volume as indicated by photoplethysmograph output signal and from the measurement of SBP and/or DBP in the calibration period, by using a constant k particular to the patient's arterial blood pressure-volume relationship, which is determined before the examination period.

Greubel et al in a US patent (U.S. Pat. No. 5,237,997, 1993) described a method for continuous measurement of the mean blood pressure from the measured transit time of the PPG pulse to the earlobe, and the systolic and diastolic blood pressure are obtained by the PPG measurement of blood volume density at the ear lobe. An initial individual basic calibration of the blood pressure values is carried out by a conventional method.

Golub in two US patents (U.S. Pat. Nos. 5,865,755 and 5,857,975, 1999) described a method for the determination of systolic and diastolic blood pressure from ECG and finger PPG outputs. The arterial pressure is computed from pulse arrival time, volumetric wave shape and instantaneous heart rate for each pulse. Golub utilizes both the time difference from R-wave to the PPG pulse start and the time difference from the PPG pulse start to the 50% height point for the pressure determination.

Inukai et al. in a US patent (U.S. Pat. No. 6,527,725, 2003) described a method for the determination of arterial blood pressure from pulse transit time and from at least one of the parameters HR and pulse-wave-area, after calibration by cuff-based blood pressure meter and multiple regression analysis.

Smith in European Patent Document 0 443 267 A 1 describes a technique for continuous, noninvasive measurement of blood pressure based on two PPG sensors applied to the subject's ear lobe and finger. The sensors are used for determining changes in the arrival time of the pulse at each of these sites, and to determine changes in local blood volume. Following an initial calibration using pressure measurement obtained with a conventional blood pressure cuff, the Smith technique adjusts these pressures by interpreting changes in the pulse transit time and in the optical density of the PPG signal.

All these techniques are not suitable for clinical blood pressure monitoring as can be deduced from the fact that no commercial device based on any of these techniques has been marketed, except that of Casio (see later), which was not accepted by the medical community because of its low accuracy. Furthermore, no information regarding examinations performed by those inventors using their techniques appears in the patent files.

Several PPG parameters are related to the pressure pulse reflections from distal sites in the arteries, where vascular impedance change occurs. PPG waveform enables the derivation of the augmentation index and second derivative parameters, which are related to the pressure wave reflection (S C Millaseau et al. Hypertension 36:952-956, 2000 and K Takazawa et al. Hypertension 32:365-370, 1998). Analysis of the PPG signal during the diastolic decrease period was suggested by Cohn (U.S. Pat. No. 5,054,493). Akselrod et al. in (U.S. Pat. No. 6,280,390, 2001) used spectral analysis of the PPG pulses obtained by more than one probes for the determination of the arterial blood pressure. These parameters are related to the reflections from the whole body and are therefore expected to have higher correlation with systemic arterial blood pressure than local parameters such as fingertip blood volume increase during systole or pulse wave velocity in a given artery. However the accuracy and repeatability of the systemic parameters derived through the various analytical techniques were not found high enough for blood pressure monitoring.

Background of the Proposed Technique

Cuffless Measurement of Cardiovascular Parameters

Several cardiovascular parameters, such as stroke volume, conduit arteries stiffness and arteriolar resistance are involved in the determination of arterial blood pressure: the latter increases when each of these parameters increases. These cardiovascular parameters are affected by long-term structural physiological factors such as aging and atherosclerosis and in the short term are modulated through the activity of the autonomic nervous system and several biochemical substances. The modulation of these cardiovascular parameters is the means for short-term regulation of the arterial blood pressure and for selective diversion of blood flow to different organs, which are required in various physiological situations.

Though direct noninvasive measurement of stroke volume, conduit arteries stiffness and arteriolar resistance is difficult, several noninvasive techniques provide parameters which are closely related to these cardiovascular parameters and consequently to arterial blood pressure. In particular PPG—the measurement through optical means of the cardiac-induced pulsatile changes in tissue blood volume—can provide information regarding the big arteries stiffness and arteriolar resistance. The time delay of the PPG pulse in a distal site relative to that in a proximal site or relative to the R-wave of the ECG signal enable the evaluation of the pulse wave velocity, which is closely related to arterial stiffness. The amplitude of the PPG signal divided by its baseline (AM/BL) is proportional to the amplitude of the blood volume increase during systole, which is related to the small arteries compliance. The latter is inversely related to the arteriolar resistance because higher activity of the sympathetic nervous system increases arteriolar resistance and decreases arterial compliance.

Several PPG parameters are correlated with SBP and can therefore be used for the evaluation of SBP (The PPG parameters are also correlated with DBP, but the correlation is lower than that for SBP). In a study described in a paper of Nitzan et al. (Med. Biol. Eng. Comput. 37: 54-58, 1999) the very low frequency (VLF) fluctuations of SBP had correlation coefficient of −0.81 and 0.83 with the VLF fluctuations of the PPG amplitude (AM) and PPG baseline (BL), respectively, during 10 minute examinations. The VLF fluctuations in the BL parameter were delayed by about 5 heart beats relative to SBP fluctuations. The heart period also significantly correlated with SBP and DBP, but the correlation was not always of the same sign. For most of the subjects the correlation was negative, but for two subjects positive correlation was found.

Though the coefficients of correlation between SBP or DBP and the PPG parameters were statistically significant, they were not high enough for the determination of SBP in the accuracy required by clinicians. Furthermore, the high correlation between SBP or DBP and the PPG parameters was obtained after trend removal. Also note that high correlation between PPG parameters and SBP is not enough and suitable calibration is required in order to derive SBP value in absolute terms.

In another paper (Nitzan et al. Physiological Measurement 23: 85-93, 2002), the time-delay of the arrival of the PPG pulse to the toe relative to that to the finger was found to correlate with SBP (r=−0.515). The time-delay of the arrival of the PPG pulse to the toe relative to the ECG R-wave was also found to correlate with SBP (r=−0.67). The correlation between SBP and the time-delay is because both parameters depend on arterial stiffness: for higher arterial stiffness SBP increases and the time delay decreases because pulse wave velocity increases in stiffer arteries.

The correlation coefficients in the latter study are relatively low because the measurements were performed on different persons, each having different arterial structure. Arterial stiffness depends on arterial structural factors, say atherosclerosis and aging, and on short-term physiological factors such as sympathetic nervous system activity and biochemical substances in the blood. If SBP of a specific person is measured by some accurate method based on pressure cuff, simultaneously with pulse transit time (PTT) measurement, then subsequent changes in PTT will provide assessment of changes in SBP with higher correlation, since they are based on the initial calibration by the cuff-based method. Casio Company (U.S. Pat. No. 5,316,008) manufactured a watch-like blood pressure meter, based on the measurement of the time-delay between R-wave ECG and PPG signal on the wrist, and initial calibration by sphygmomanometry. The technique was not found accurate enough for clinical use.

In a recent study PPG and blood pressure examinations were performed on 11 male subjects in sitting position. Continuous blood pressure was measured on the finger by Finapres (Ohmeda, USA) finger blood pressure beat-to-beat monitor and PPG was continuously measured on the finger and ear lobe. From the Finapres monitor SBP, DBP, mean blood pressure (MBP) and the pulse pressure (PP=SBP−DBP) were derived for each pulse. From the PPG signals the following parameters were derived for each pulse: AM/BL, BL, heart period (P) and time-delay (TD) between the arrival-time of the PPG pulses in ear lobe and finger. For all persons AM/BL and TD showed inverse correlation with SBP while BL was directly related to SBP. For some examinations the heart period directly correlated with SBP, but for other examinations inverse relationship between the two parameters was found. Using linear multi-regression analysis the coefficient of correlation between SBP and the four PPG parameters was found to be 0.61-0.95. The mean RMSE value, which is equivalent to standard deviation between the Finapres measurement of SBP and the derivation of SBP from the linear multi-regression formula was 9.5 mmHg, which is not far from the requirements of AAMI for automatic cuff-based blood pressure meters, say standard deviation of 8 mmHg.

AM/BL is inversely related to SBP because AM/BL is proportional to the amplitude of the heart-induced blood volume pulse, which increases with the compliance of the small arteries in the tissue. Since higher tonus of the arterial wall muscles decreases the compliance of the small arteries while increasing SBP (by increasing arteriolar resistance), SBP and AM/BL are inversely related. The tonus of the arterial wall muscles is affected by the sympathetic nervous system and by blood biochemical substances. From changes in AM/BL, PTT and other PPG based parameters, such as heart period, changes in SBP can be predicted.

In this study we also compared the start time of the VLF fluctuations of AM/BL in comparison to the VLF fluctuations of the other parameters. We have found that on the average the VLF fluctuations of the heart period P and the finger-ear time-delay TD preceded the AM/BL VLF fluctuations by 4 pulses and 3 pulses, respectively, and the BL VLF fluctuations lagged the AM/BL VLF fluctuations by 6 pulses. These timing differences are important since in determining changes in SBP from changes in several parameters one has to use the value of each parameter in the appropriate pulse.

SUMMARY OF THE INVENTION

Figure Captions

FIG. 1. The curves of the PPG and the cuff pressure as a function of time for one of the subjects. The PPG pulses reappear when the cuff pressure decreases to below systolic blood pressure. The systolic blood pressure as obtained by sphygmomanometry (SBPS) and the corresponding time are marked by dashed lines.

Figure 2:
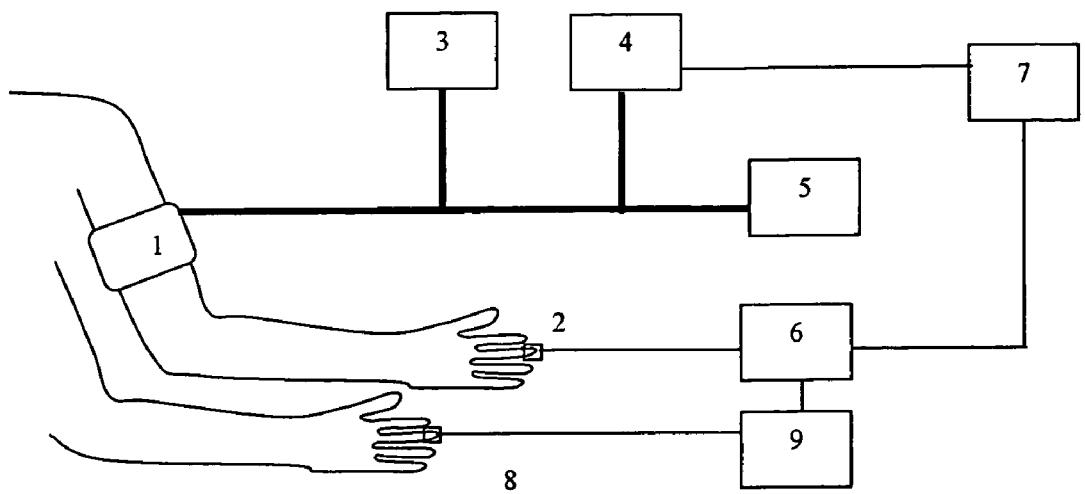

FIG. 2. Schematic drawing of the cuff-based calibration in the cuffless blood pressure measurement system: 1. Pressure cuff. 2. PPG probe in a finger distal to the pressure cuff. 3. Mercury manometer (optional). 4. Piezoelectric transducer. 5. Pressure pump and its electronic control. 6. Electronic control of the distal PPG probe. 7. Digital analysis of the PPG and piezoelectric transducer signals. 8. PPG probe in a the finger in a free hand. 9. Electronic control of the free-hand PPG probe.

Figure 3:
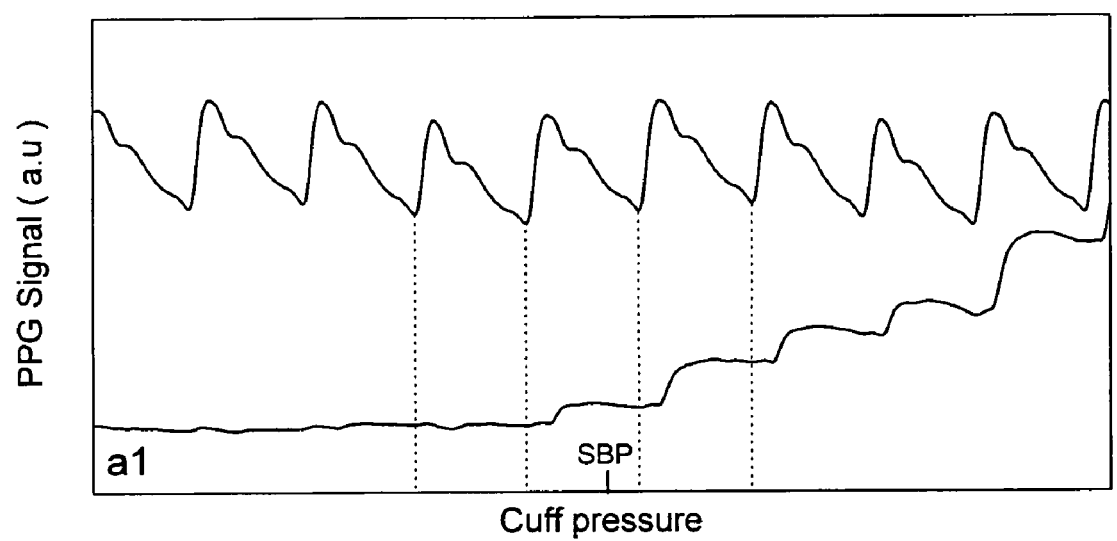

FIG. 3. The curves of the PPG signals in the probe distal to the cuff (below) and in the free hand (above) for cuff pressure in the neighborhood of SBP. The PPG signals to the cuff are delayed relative to PPG signals in the free hand.

Figure 4:
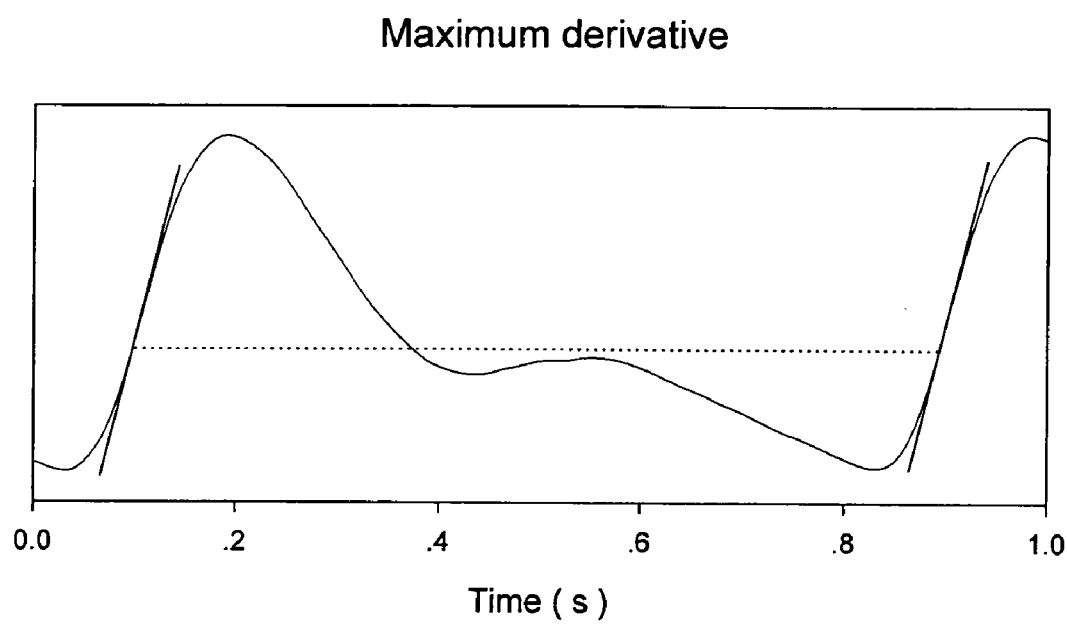

FIG. 4. A PPG pulse demonstrating the point of maximum derivative, and the line connecting the point of maximum derivative in the pulse with the point of maximum derivative in the next pulse.

Figure 5:
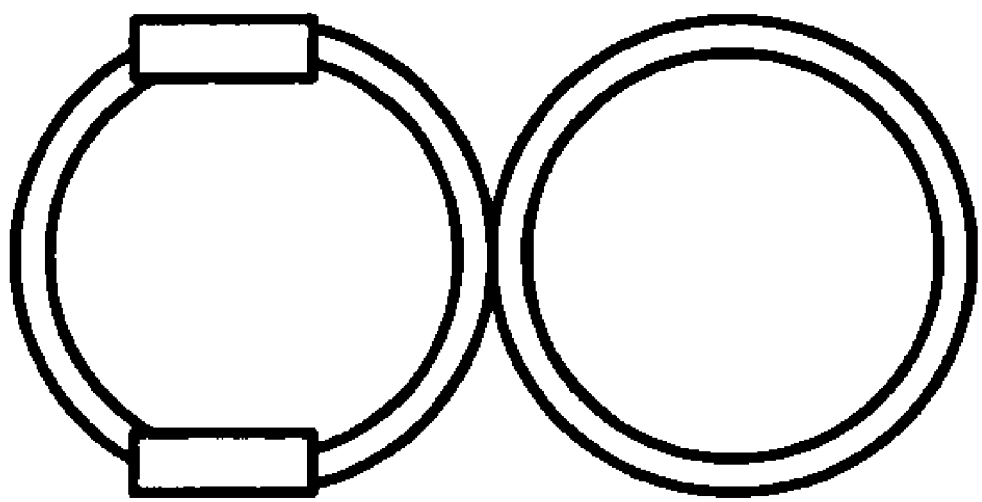

FIG. 5. Two connected rings with a PPG probe embedded in one of them for reproducible PPG measurement after removing the probe from the fingers and replacing it.

The method for cuffless monitoring of SBP is based on two simultaneous measurements of PPG, using two PPG sensors, one of which is more distal than the other relative to the heart. The signal of at least one PPG sensor is used to derive AM/BL, which is related to the increase of tissue blood volume during systole, in order to assess the effects of the sympathetic nervous system and the blood biochemical substances on the tissue small arteries and arterioles. The other sensor is used, together with the first sensor, to derive the time-delay (TD) in the arrival time between the two PPG probes, which is inversely related to the pulse wave velocity in the conduit arteries. A preferred body-site for the placement of the other sensor is the ear-lobe. Both pulse wave velocity and SBP increase when the big conduit arteries walls become less compliant (more rigid).

In order to obtain SBP values, several initial measurements of the PPG parameters must be accompanied with measurements of SBP through a cuff-based method, for calibration. The simultaneous measurement of SBP for calibration is preferably performed by the automatic cuff-based and PPG-based method described above (see FIG. 1), because it is both accurate and automatic. The system for calibration of the PPG parameters is described in FIG. 2, which includes the PPG probes in the finger distal to the cuff and in the free hand, but does not show the PPG probe in the earlobe.

The invention preferably includes averaging of AM/BL, TD and P over time periods, each of which includes at least 4-12 pulses, both in the calibration process and in the monitoring. These time periods are long enough to reduce the effects of short-term spontaneous fluctuations in AM/BL, P and TD in the respiratory rate (the high-frequency spontaneous fluctuations) and in the low-frequency region of about 0.1 Hz, while keeping the effect of the very-low-frequency spontaneous fluctuations. The group of 4-12 pulses, which is used for the determination of the average value of P, is lagged by 4-6 pulses relative to the group used for the determination of the average value of AM/BL.

In another aspect of the invention, the group of 4-12 pulses, which is used for the determination of the average value of AM/BL, is lagged by 2-5 pulses relative to the group used for the determination of the average value of TD.

In another aspect of the invention, the value of the systolic blood pressure (SBP) used for calibration is also taken as the mean of at least three measurements in order to reduce the effects of the high-frequency spontaneous fluctuations. An automatic cuff-based blood-pressure meter measures at least three times the value of SBP of the person, by inflating the cuff to air pressure slightly above SBP value and slowly deflating the cuff, and simultaneously measuring the light intensity in the photodetector of a PPG probe located distal to the cuff, in order to automatically detect the disappearance of the PPG signal during the cuff inflation to above SBP value and the reappearance of the PPG signal during the slow cuff deflation.

In another aspect of the invention, the automatic detection of the disappearance of the PPG signal during the inflation periods and the reappearance of the PPG signal during the deflation periods is done by division of the output of the distal-to-the-cuff detector into segments. Each segment is expected to include full PPG pulse if PPG pulse appears at the corresponding time. The presence of a PPG pulse is verified by calculation of two parameters characterizing PPG pulses in each segment: a pulse pattern parameter and the correlation of the signal in each segment with the signal in the neighboring segment.

In another aspect of the invention, the time segments of the detector output in the PPG sensor distal to the cuff, each of which is expected to include full PPG pulse if PPG pulse appears at the corresponding time, are determined through the corresponding pulse in the PPG signal in the other hand, taken from minimum point $t_{MNF}$ (the time point in which the systolic increase of the PPG pulse starts) to next minimum point. Because the PPG pulse distal to the cuff is delayed relative to the PPG pulse in the other hand, the minimum of the former is searched in the region of 50-120 ms after $t_{MNF}$ in the latter. For each PPG pulse in the free hand, the time-point $t_{MNF}$ of the pulse minimum is found, and in its neighborhood (from $t_{MNF}$+50 ms to $t_{MNF}$+120 ms) the time-point of the minimum of the output of the PPG sensor distal to the cuff is determined (FIG. 3)

In another aspect of the invention, the time segments of the PPG signals are taken from the time point of maximum derivative to the next time point of maximum derivative (FIG. 4).

In another aspect of the invention, the pulse pattern is determined by subtracting the line connecting the point of the maximum derivative of the pulse to the next maximum derivative point from the output of the PPG sensor distal to the cuff (see FIG. 4), and calculating the integral of the difference between the said output and the said line, for the first half (INT1) and for the second half (INT2) of the segment. The difference between the integral values for the two halves (INT1−INT2) is taken as pulse pattern parameter PPP. For normal PPG pulse INT1 is positive and INT2 is negative so that PPP=INT1−INT2 is positive. If the signal is composed of random noise PPP is zero.

In another aspect of the invention, the correlation coefficient (CC) is calculated for each segment in the PPG curve in the finger distal to the cuff between the signal in the segment and the signal in each neighboring segment. The preferable borders of the segments for the integration are the two time-points of $t_{DMX}$, but minimum points can be used as well. If CC is higher than a predetermined value the signal is considered as PPG pulse.

Because the correlation function requires two equal-length arrays, the length of the two segments to be correlated must be equal. If the two segments are not equal the longer one is rarefied (diluted) by eliminating the required number of sampling points of it. The signal in each segment undergoes operations of 'smoothing' (moving average of 11 points: 5+1+5) and 'detrending' (subtraction of the line from the first point of the segment to the last point from the signal). Then CC is calculated between each segment and its two neighboring segments and the higher value of the two CC values is taken as the final value, which represents the correlation of the segment with its neighbors.

In this stage, the values of PPP and CC for each pulse are used for the determination of the first PPG pulse, which appears during the cuff deflation.

Firstly, the average value of PPP for the hand distal to the hand before the inflation ($PPP_{IN}$) is calculated. Then the first PPG pulse is taken as the first of seven consecutive segments, which comply with one of the two conditions:
1. At least five segments have CC value higher than 0.85, and PPP value higher than 1% of $PPP_{IN}$.
2. At least five segments have CC value higher than 0.65, and for three of them PPP value is higher than 7% of $PPP_{IN}$. For the other two segments PPP value is higher than 10% of $PPP_{IN}$.

The SBP value is the value of the cuff pressure corresponding to the first PPG pulse of the seven segments which satisfies the corresponding CC and/or PPP requirements.

It will be appreciated that the above criteria are given as a preferred example, but may be varied considerably within the scope of the present invention. Thus, in more general terms, the restart of the pulse is identified by satisfying either, or preferably both, of a correlation condition relative to the reference signal and an independently defined pulse shape condition in at least n segments out of m consecutive segments where $n \leq m$.

In another aspect of the invention the finger PPG signal is measured by a sensor, comprised of a light source and a detector, embedded in a ring-like device, which is connected to another ring (FIG. 5), so that the two rings are put on two adjacent fingers, in order that the PPG light source and detector will be attached to the same tissue, even after placing back the sensor after removing it from the finger.

It should be noted that assessment of changes in PTT can be done by the time-delay between two PPG probes, as described above, but it can also be done by a different pulse-detecting sensor instead of at least one PPG sensor, or by ECG recording and PPG sensor (or another pulse-detecting sensor).

It should also be noted that, similar to the technique for SBP monitoring, DBP or PP (pulse pressure) can also be monitored by appropriate measurement of PPG parameters after initial calibration through several cuff-based measurements of DBP or PP.

The invention claimed is:

1. An automatic cuff-based blood-pressure measuring device for measuring the systolic blood pressure (SBP) of a subject, the device comprising:
    a pressure cuff for wrapping around an arm of the subject;
    a photoplethysmographic (PPG) sensor for generating an output signal indicative of arterial blood volume change induced by heart beat of the subject, said PPG sensor being adapted for attachment to skin of the subject in a first peripheral site distal to the middle of the pressure cuff;
    an electrically controlled pump for inflating and deflating the cuff; and
    a second sensor for attachment to the skin in a second peripheral site which is not distal to the middle of the pressure cuff and which produces an output indicative of a second hemodynamic parameter related to the heart beat;

wherein the device is configured to:
(a) activate said pump to inflate said cuff, automatically detect the disappearance of a pulse from said PPG signal, and activate said pump to slowly deflate said cuff;
(b) derive from the second hemodynamic parameter signal the arrival time of each pulse; and
(c) during said deflation, automatically detect the reappearance of the PPG signal, wherein the automatic detection of reappearance of the PPG signal during the deflation periods includes defining time segments, based upon said arrival time of each pulse as derived from said second sensor, during which a full PPG pulse of a reappearing PPG pulse in the output of said PPG sensor would be expected to occur, and applying a decision algorithm which determines whether a PPG pulse appears in time segments of the output of said PPG sensor, where said decision algorithm includes calculation of at least one of the following two parameters characterizing PPG pulses in each segment: a pulse pattern parameter and the correlation of the signal in each segment with the signal in the neighboring segments.

2. The device as in claim 1, wherein said time segments are defined as segments of a predetermined length starting with a given delay relative to time points $t_{MNF}$ of the second sensor pulses, wherein time points $t_{MNF}$ correspond to the start of a systolic change of the second sensor pulse.

3. The device as in claim 1, where said second sensor is a PPG sensor.

4. The device as in claim 3, where the two sensors are adapted for attachment to fingers in two hands of the subject and said time segments for detection of a reappearing pulse in said PPG signal from said sensor distal to the cuff are defined to start at a delay of at least 50 milliseconds after arrival of the pulse as detected by said second sensor and finishing at least 120 ms after arrival of the pulse.

5. The device as in claim 1, where said second sensor is a pressure sensor, which measures the air pressure pulsations in the pressure cuff.

6. The device as in claim 1, wherein said time segments are defined as segments of a predetermined length starting with a given delay relative to a time point of maximum derivative $t_{DMXF}$ of the second sensor pulses.

7. The device as in claim 6, wherein said time segments for detection of a reappearing pulse in said PPG signal from said sensor distal to the cuff are defined to start at a defined delay relative to the time-points $t_{DMXF}$ of the maximum derivative points of the PPG pulses from said second sensor.

8. The device as in claim 7, wherein said defined delay is at least 50 milliseconds.

9. The device as in claim 1, where said pulse pattern is determined by subtracting the line connecting the point of the maximum derivative of the pulse to the next maximum derivative point from the output of the PPG sensor distal to the cuff, and calculating the integral of the difference between said output and said line for the first half (INT1) and the second half (INT2) of the segment, and the difference between the integral values for the two halves (INT1−INT2) is taken as pulse pattern parameter (PPP).

10. The device as in claim 1, where the correlation of the signal in each segment with the signal in the neighboring segment is performed after eliminating sampling points from the longer segment if the two segments are not equal.

11. The device as in claim 9, where the average value of PPP for the hand distal to the cuff before the inflation ($PPP_{IN}$) is calculated, and the first PPG pulse is taken as the first of a predetermined number of consecutive segments in which at least one of the following conditions is fulfilled for at least a predetermined fraction of said predetermined number of consecutive segments: the correlation coefficient value is higher than a predetermined specific value, and the PPP value is higher than a predetermined specific fraction of $PPP_{IN}$.

12. The device as in claim 11, where said predetermined specific value is in the region of 0.65-0.85, and said predetermined specific fraction of $PPP_{IN}$ is in the region of 1-10% of $PPP_{IN}$.

13. An automatic cuff-based blood-pressure measuring method for measuring the systolic blood pressure (SBP) of a subject, the method comprising the steps of:
providing a pressure cuff for wrapping around an arm of the subject;
providing a photoplethysmographic (PPG) sensor for generating an output signal indicative of arterial blood volume change induced by heart beat of the subject, said PPG sensor being adapted for attachment to skin of the subject in a first peripheral site distal to the middle of the pressure cuff;
providing an electrically controlled pump for inflating and deflating the cuff;
providing a second sensor for attachment to the skin in a second peripheral site which is not distal to the middle of the pressure cuff and which produces an output indicative of a second hemodynamic parameter related to the heart beat;
activating said pump to inflate said cuff, automatically detect the disappearance of a pulse from said PPG signal, and activate said pump to slowly deflate said cuff;
deriving from the second hemodynamic parameter signal the arrival time of each pulse; and
during said deflation, automatically detecting the reappearance of the PPG signal, wherein the automatic detection of reappearance of the PPG signal during the deflation periods includes defining time segments, based upon said arrival time of each pulse as derived from said second sensor, during which a full PPG pulse of a reappearing PPG pulse in the output of said PPG sensor would be expected to occur, and applying a decision algorithm which determines whether a PPG pulse appears in time segments of the output of said PPG sensor, where said decision algorithm includes calculation of at least one of the following two parameters characterizing PPG pulses in each segment: a pulse pattern parameter and the correlation of the signal in each segment with the signal in the neighboring segments.

14. The method as in claim 13, wherein said time segments are defined as segments of a predetermined length starting with a given delay relative to time points $t_{MNF}$ of the second sensor pulses, wherein time points $t_{MNF}$ correspond to the start of a systolic change of the second sensor pulse.

15. The method as in claim 13, where said second sensor is a PPG sensor.

16. The method as in claim 15, where the two sensors are adapted for attachment to fingers in two hands of the subject and said time segments for detection of a reappearing pulse in said PPG signal from said sensor distal to the cuff are defined to start at a delay of at least 50 milliseconds after arrival of the pulse as detected by said second sensor and finishing at least 120 ms after arrival of the pulse.

17. The method as in claim 13, where said second sensor is a pressure sensor, which measures the air pressure pulsations in the pressure cuff.

18. The method as in claim 13, wherein said time segments are defined as segments of a predetermined length starting with a given delay relative to a time point of maximum derivative $t_{DMXF}$ of the second sensor pulses.

19. The method as in claim 18, where said time segments for detection of a reappearing pulse in said PPG signal from said sensor distal to the cuff are defined to start at a defined delay relative to the time-points $t_{DMXF}$ of the maximum derivative points of the PPG pulses from said second sensor.

20. The method as in claim 19, wherein said defined delay is at least 50 milliseconds.

21. The method as in claim 13, where said pulse pattern is determined by subtracting the line connecting the point of the maximum derivative of the pulse to the next maximum derivative point from the output of the PPG sensor distal to the cuff, and calculating the integral of the difference between said output and said line for the first half (INT1) and the second half (INT2) of the segment and the difference between the integral values for the two halves (INT1−INT2) is taken as pulse pattern parameter (PPP).

22. The method as in claim 13, where the correlation of the signal in each segment with the signal in the neighboring segment is performed after eliminating sampling points from the longer segment if the two segments are not equal.

23. The method as in claim 21, where the average value of PPP for the hand distal to the cuff before the inflation ($PPP_{IN}$) is calculated, and the first PPG pulse is taken as the first of a predetermined number of consecutive segments in which at least one of the following conditions is fulfilled for at least a predetermined fraction of said predetermined number of consecutive segments: the correlation coefficient value is higher than a predetermined specific value, and the PPP value is higher than a predetermined specific fraction of $PPP_{IN}$.

24. The method as in claim 23, where said predetermined specific value is in the region of 0.65-0.85, and said predetermined specific fraction of $PPP_{IN}$ is in the region of 1-10% of $PPP_{IN}$.

* * * * *